United States Patent
Kothrade et al.

(10) Patent No.: US 7,022,344 B1
(45) Date of Patent: Apr. 4, 2006

(54) PROCESS FOR PRODUCING SOLID DOSAGE FORMS

(75) Inventors: Stephan Kothrade, Limburgerhof (DE); Gunther Berndl, Herxheim (DE); Dirk Simon, Mutterstadt (DE); Axel Sanner, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/268,719

(22) Filed: Mar. 17, 1999

(30) Foreign Application Priority Data

Mar. 23, 1998 (DE) .................................. 198 12 688

(51) Int. Cl.
*A61K 9/10* (2006.01)
*A61K 47/32* (2006.01)

(52) U.S. Cl. ................................ 424/486; 424/487

(58) Field of Classification Search .................. 424/486, 424/487, 488, 499, 501, 464; 514/772.5, 514/772.6
See application file for complete search history.

(56) References Cited

U.S. PATENT DOCUMENTS

| | | | | |
|---|---|---|---|---|
| 4,057,598 A | * | 11/1977 | Lundberg et al. | |
| 4,801,460 A | | 1/1989 | Goertz et al. | 424/465 |
| 4,880,585 A | | 11/1989 | Klimesch et al. | 264/141 |
| 4,957,681 A | | 9/1990 | Klimesch et al. | 264/211 |
| 5,073,379 A | | 12/1991 | Klimesch et al. | 424/467 |
| 5,552,159 A | | 9/1996 | Mueller et al. | 424/464 |

FOREIGN PATENT DOCUMENTS

WO 95/24430 9/1995

OTHER PUBLICATIONS

Bauer et al., *Pharm. Tech.*, Thieme–Verlag, pp. 292–295.
Ford et al., *Pharm. Acta. Helv.*, vol. 61, 1986, pp. 69–88.
Thoma et al., *Pharm. Ind.*, vol. 51, 1989, pp. 98–101.
Chen et al., *ACS Symp. Ser.*, 1997, 680 (poly(ethyleneglycol)), 441–457.

* cited by examiner

*Primary Examiner*—Edward J. Webman
(74) *Attorney, Agent, or Firm*—Keil & Weinkauf

(57) ABSTRACT

A process for producing solid dosage forms by mixing at least one polymer binder, at least one active ingredient and, where appropriate, conventional additives to form a plastic mixture, and shaping, wherein a physiologically tolerated, water-swellable graft copolymer or a mixture of graft copolymers is employed as polymeric binder.

10 Claims, No Drawings

PROCESS FOR PRODUCING SOLID DOSAGE FORMS

The invention relates to a process for producing solid dosage forms by mixing at least one polymeric binder and, where appropriate, at least one active ingredient and, where appropriate, conventional additives to form a plastic mixture, and shaping. The invention particularly relates to a process for producing solid pharmaceutical forms.

Classical processes for producing solid pharmaceutical forms, especially tablets, are carried out batchwise and comprise a plurality of stages. Pharmaceutical granules represent an is important intermediate therefor. Thus, for example, Bauer, Frömmig and Führer, "Pharmazeutische Technologie", Thieme Verlag, pages 292 et seg., reveal that drug forms can be obtained from the melt by dry granulation. The possibility of producing solidified melt granules either by melting and shock solidification, by casting and comminuting or by prilling in spray towers is described. One problem with these processes is the accurate shaping which is necessary for producing drugs. Irregular particles or fragments are often produced, so that the resulting shape by no means corresponds to customary drug forms, and granules therefore have only little importance as a drug form on their own. Production of desired solid drug forms requires the use of further process steps such as compression in tabletting machines. This is time-consuming and costly.

A considerably simpler continuous process for producing solid pharmaceutical forms has been known for some time and entails extruding a solvent-free melt of a polymeric binder containing active ingredients, and shaping the extrudate to the required drug form, for example in a calender with molding rolls, see EP-A-240 904, EP-A-240 906, EP-A-337 256, U.S. Pat. No. 4,880,585 and EP-A-358 105. It is possible in this way to achieve specific shaping. The polymeric binders employed are, in particular, polymers of N-vinylpyrrolidone or copolymers thereof, eg. with vinyl acetate.

Dosage forms based on polymers of this type have the disadvantage that they release the active ingredient relatively quickly. It is therefore impossible to produce slow-release dosage forms without taking additional measures, for example applying a release-controlling coating.

It is an object of the present invention to provide dosage forms which can be produced by melt extrusion and are capable of slow release of active ingeient.

We have found that this object is achieved by using a physiologically tolerated, water-swellable graft copolymer as polymeric binder.

The present invention therefore relates to a process for producing solid dosage forms by mixing at least one polymer binder, at least one active ingredient and, where appropriate, conventional additives to form a plastic mixture, and shaping, wherein an in particular physiologically tolerated, water-swellable graft copolymer or a mixture of graft copolymers is employed as polymeric binder.

The novel process makes it possible to produce solid dosage forms with very slow release of active ingredient ("sustained release", "slow release") in a simple and cost-effective manner. Another surprising advantage of the novel process is that it is also possible, owing to the low glass transition temperature of the graft copolymers which can be employed (<90° C.), to prepare formulations of temperature-sensitive active ingredients under mild conditions. It is moreover possible to adjust the rate of release within a wide range by admixing polymers with rapid release, such as polyvinylpyrrolidone; copolymers of polyvinylpyrrolidone and vinyl acetate; cellulose ethers such as hydroxypropylcellulose or hydroxyethylcellulose; polyethylene glycols or ethylene oxide/propylene oxide-block copolymers (e.g. the pluronic brands of BASF AG); polyvinyl alcohols; partially hydrolyzed polyvinyl alcohols or suitable low molecular weight substances such as sugar alcohols, sugars or salts.

Dosage forms mean herein all forms which are suitable for use as drugs, plant treatment compositions, human and animal foods and for delivering fragrances and perfume oils. These include, for example, tablets of any shape, pellets, granules, but also larger forms such as cubes, blocks (bricks) or cylindrical forms, which can be used, in particular, as human or animal foods.

The dosage forms obtainable according to the invention generally comprise:

I 0–90% by weight, in particular 0.1–60% by weight (based on the total weight of the dosage form) of an active ingredient, II 10–100% by weight, in particular 40–99.9% by weight, of the polymeric binder and III where appropriate additives.

The polymers used according to the invention as binders are obtainable in a manner known per se by free-radical polymerization. Preparation takes place, for example, by solution, precipitation, suspension or emulsion polymerization using compounds which form free radicals under the polymerization conditions. It is preferred to employ in the novel process a graft copolymer obtainable by polymerization, initiated by free radicals, of a) a component selected from a1) $C_1$–$C_{30}$-alkyl esters of an α,β-monoethylenically unsaturated $C_3$–$C_{30}$-mono- or dicarboxylic acid. The $C_1$–$C_{18}$-, in particular the $C_1$–$C_8$-, alkyl esters of these acids are preferred. Of these acids, the $C_3$–$C_8$-mono- or dicarboxylic acids are preferred, such as acrylic acid, methacrylic acid, dimethylacrylic acid, ethacrylic acid, maleic acid, citraconic acid, methylenemalonic acid, crotonic acid, fumaric acid, mesaconic acid and itaconic acid, with acrylic acid and methacrylic acid being particularly preferred, a2) $C_2$–$C_4$-hydroxyalkyl esters of the acids mentioned under a1), a3) amides, mono- or di-$C_1$–$C_4$-alkylamides and nitriles of the carboxylic acids mentioned under a1), a4) vinyl esters of $C_1$–$C_{18}$-monocarboxylic acids and a5) vinylaromatic compounds, in particular styrene, b) oxygen-containing, preferably hydroxyl-containing polymers, in particular also containing alkylene oxide units, as grafting base and c) where appropriate a monomer which has at least two nonconjugated ethylenically unsaturated double bonds.

It is also possible to employ a mixture of monomers a). It is furthermore possible for the monomers a) to comprise up to 5% by weight, based on the total amount of monomers a), of an α,β-monoethylenically unsaturated $C_3$–$C_8$-carboxylic acid, in particular acrylic acid or methacrylic acid.

It is possible to employ as monomers a) for preparing the graft copolymers in particular methyl acrylate, ethyl acrylate, methyl methacrylate, ethyl methacrylate, hydroxyethyl acrylate, hydroxypropyl acrylate, hydroxybutyl acrylate, hydroxyethyl methacrylate, hydroxypropyl methacrylate, hydroxyisobutyl acrylate, hydroxyisobutyl methacrylate, monomethyl maleate, dimethyl maleate, monoethyl maleate, diethyl maleate, 2-ethylhexyl acrylate, 2-ethylhexyl methacrylate, stearyl acrylate, stearyl methacrylate, behenyl acrylate, behenyl methacrylate, octyl acrylate, octyl methacrylate, acrylamide, methacrylamide, N-dimethylacrylamide, N-tert-butylacrylamide, acrylonitrile, methacrylonitrile, and vinyl acetate, vinyl propionate and styrene or mixtures thereof. Particularly preferred components a) are methyl acrylate, ethyl acrylate, methyl methacrylate, ethyl methacrylate, n-butyl acrylate, tert-butyl acrylate or mixtures thereof.

The grafting bases are preferably selected from:
b1) polymers-containing alkylene oxide units. These include homo- and copolymers of $C_2$–$C_4$-alkylene oxides, polytetrahydrofurans, the products of the reaction of $C_2$–$C_4$-alkylene oxides with $C_1$–$C_{30}$-alcohols, fatty acids, $C_1$–$C_{12}$-alkylphenols, primary or secondary aliphatic $C_2$–$C_{30}$-amines, or mixtures thereof;
b2) polyvinyl alcohols or copolymers of polyvinyl alcohol (PVA) and vinyl acetate (VA) (partially hydrolyzed polyvinyl acetate), preferably in the PVA:VA ratio of 95:5 to 10:90 by weight;
b3) starch, cellulose and derivatives thereof, such as methylcellulose, hydroxyethylcellulose, hydroxypropylmethylcellulose and carboxymethylcellulose.

The copolymers of $C_2$–$C_4$-alkylene oxides may be either random copolymers, when mixtures of at least 2 alkylene oxides are polymerized, or block copolymers, when firstly one alkylene oxide, for example ethylene oxide, is polymerized and then another alkylene oxide is polymerized, e.g. propylene oxide. The block copolymers may, for example, belong to the AB, ABA or BAB type, where A can be, for example, a polyethylene oxide block and B can be a polypropylene oxide block. These copolymers may also, where appropriate, contain n-butylene oxide and/or isobutylene oxide units. The polyalkylene oxides contain at least three alkylene oxide units in the molecule. The polyalkylene oxides can have, for example, up to 50 000 alkylene oxide units in the molecule. The polytetrahydrofurans contain, for example, 3 to 200, preferably 3 to 100, tetramethylene oxide units.

Compounds b) which are particularly preferably employed are, besides the abovementioned homo- or block copolymers of ethylene oxide and propylene oxide, also ethylene oxide/propylene oxide copolymers with a random structure, and polyvinyl alcohol.

Examples of suitable alcohols for the products of the reaction of alkylene oxides with alcohols ($C_1$–$C_{30}$-alcohols) are aliphatic monoalcohols such as methanol, ethanol, n-propanol, isopropanol, n-butanol, n-octanol, 2-ethylhexanol, decanol, dodecanol, palmityl alcohol, cetyl alcohol and stearyl alcohol. However, it is also possible to employ dihydric and polyhydric aliphatic alcohols, e.g. glycol, glycerol, erythritol, pentaerythritol and sorbitol. The alcohols are reacted in the molar ratio of 1:3 to 1:200 with at least one $C_2$–$C_4$-alkylene oxide.

Further suitable polymers b1) containing alkylene oxide units are products of the reaction of fatty acids with alkylene oxides. Particularly suitable fatty acids are those which contain 8 to 10 C atoms in the molecule, for example lauric acid, myristic acid, stearic acid, palmitic acid, coconut fatty acid, tallow fatty acid and oleic acid.

Polymers b1) containing alkylene oxide units are moreover the products of the addition of $C_2$–$C_4$-alkylene oxides onto $C_1$–$C_{12}$-alkylphenols such as n-cetylphenol, n-octylphenol, isobutylphenol and methylphenol. Also suitable as component b) for preparing the graft copolymers are the products of the addition of $C_2$–$C_4$-alkylene oxides onto primary and secondary $C_2$–$C_{30}$-amines such as di-n-butylamine, di-n-octylamine, dimethylamine and distearylamine. The molar ratio of amine to alkylene oxide is from 1:3 to 1:200, and is preferably in the range from 1:3 to 1:100. For preparing the adducts of alkylene oxides and alcohols, phenols, acids or amines, it is possible to add the alkylene oxides in a known manner onto the abovementioned compounds simultaneously and successively. Successive addition of alkylene oxides results in block copolymers. It may in some cases also be advantageous to cap the free OH groups of the alkoxylation products with an endgroup. Endgroup capping can take place, for example, with an alkyl radical to form an ether group. For example, the alkoxylation products can be reacted with an alkylating agent such as dimethyl sulfate. The terminal OH groups can also be esterified where appropriate by reacting with carboxylic acids, e.g. acetic acid or stearic acid.

The graft copolymers can be modified by copolymerizing the monomers or monomer mixtures of component a) with up to 5% by weight, preferably 0.05 to 2% by weight, of one or more monomers of component c) which have at least two nonconjugated ethylenically unsaturated double bonds in the molecule in the presence of component b). The components c) are normally used as crosslinkers in copolymerizations. Examples of suitable components c) are methylenebisacrylamide, divinylethyleneurea, esters of acrylic acid and methacrylic acid with polyhydric alcohols, such as glycol diacrylate, glycerol triacrylate, glycol dimethacrylate, glycerol trimethacrylate, and polyols esterified at least twice with acrylic acid and methacrylic acid, such as pentaerythritol and glucose. Suitable crosslinkers which can also be employed as component c) are divinylbenzene, divinyldioxane, pentaerythritol triallyl ether and pentaallylsucrose.

Components a) and b) are preferably employed in a ratio by weight in the range from 95 to 10:5 to 90, in particular 85 to 55:15 to 45.

The polymerization temperatures for producing the graft copolymers which can be employed according to the invention are normally in the range from 30 to 200° C., preferably 40 to 110° C. Examples of suitable initiators are conventional azo and peroxy compounds, and conventional redox initiator systems such as combinations of hydrogen peroxide and reducing compounds, for example sodium sulfite, sodium bisulfite, sodium formaldehyde sulfoxylate and hydrazine.

The graft copolymerization can also be carried out by exposure to ultraviolet radiation, where appropriate in the presence of UV initiators. Employed for polymerization with exposure to UV rays are the photoinitiators and sensitizers normally considered for this purpose, such as benzoin and benzoin ethers, α-methylbenzoin or α-phenylbenzoin. It is also possible to use triplet sensitizers such as benzil diketals. Examples of sources of UV radiation used are, beside high-energy UV lamps such as carbon arc lamps, mercury vapor lamps or xenon lamps, also low-UV light sources such as fluorescent tubes with a high blue content.

The usual regulators can be employed to obtain low molecular weights, for example compounds which contain sulfur in bound form, such as alkyl mercaptans.

The homo- and copolymers generally have K values of at least 7, preferably from 10 to 100, in particular 20 to 100, particularly preferably 20 to 35. The K values are determined by the method of H. Fikentscher, Cellulosechemie, volume 13, 58–64 and 71–74 (1932), in aqueous solution or in an organic solvent at 25° C. and with concentrations between 0.1% and 5%, depending on the K value range.

Besides the polymeric binders which can be employed according to the invention and are described above, it is possible to employ in particular up to 30% by weight, based on the total weight of the binder, of other binders such as polymers, copolymers, cellulose derivatives, starch and starch derivatives. Suitable examples are:

Polyvinylpyrrolidone (PVP), copolymers of N-vinylpyrrolidone (NVP) and vinyl esters, in particular vinyl acetate, copolymers of vinyl acetate and crotonic acid, partially hydrolyzed polyvinyl acetate, polyvinyl alcohol, poly(hydroxyalkyl acrylates), poly(hydroxyalkyl methacrylates), polyacrylates and polymethacrylates (Eudragit types), copolymers of methyl methacrylate and acrylic acid, polyacrylamides, polyethylene glycols, cellulose esters, cellulose ethers, especially methyl cellulose and ethyl cellulose, hydroxyalkylcelluloses, especially hydroxypropylcellulose, hydroxyalkylalkylcelluloses, especially hydroxypropylethylcellulose, cellulose phthalates, especially cellulose acetate phthalate and hydroxypropylmethylcellulose phthalate, and mannans, especially galactomannans. Of these, polyvinylpyrrolidone, copolymers of N-vinylpyrrolidone and vinyl esters, poly(hydroxyalkyl acrylates), poly(hydroxyalkyl methacrylates), polyacrylates, polymethacrylates, alkylcelluloses and hydroxyalkylcelluloses are particularly preferred.

The polymeric binder which can be employed according to the invention must soften or melt in the complete mixture of all the components in the range from 50 to 180° C, preferably 60 to 130° C. The glass transition temperature of the mixture must therefore be below 180° C., preferably below 130° C., in particular below 90° C. If necessary, it is reduced by conventional pharmacologically acceptable plasticizing auxiliaries. The amount of plasticizer does not exceed 30% of the total weight of binder and plasticizer in order to form storage-stable drug forms which show no cold flow. However, the mixture preferably contains no plasticizer.

Examples of such Plasticizers are:

long-chain alcohols, ethylene glycol, propylene glycol, glycerol, trimethylolpropane, triethylene glycol, butanediols, pentanols such as pentaerythritol, hexanols, polyethylene glycols, polypropylene glycols, polyethylene/propylene glycols, silicones, aromatic carboxylic esters (eg. dialkyl phthalates, trimellitic esters, benzoic esters, terephthalic esters) or aliphatic dicarboxylic esters (eg. dialkyl adipates, sebacic esters, azelaic esters, citric and tartaric esters), fatty acid esters such as glycerol mono-, di- or triacetate or sodium diethyl sulfosuccinate. The concentration of plasticizer is generally from 0.5 to 15, preferably 0.5 to 5, % of the total weight of the mixture.

Conventional pharmaceutical auxiliaries, whose total amount can be up to 100% of the weight of the polymer, are, for example, extenders and bulking agents such as silicates or diatomaceous earth, magnesium oxide, aluminum oxide, titanium oxide, stearic acid or its salts, eg. the magnesium or calcium salt, methylcellulose, sodium carboxymethylcellulose, talc, sucrose, lactose, cereal or corn starch, potato flour, polyvinyl alcohol, in particular in a concentration of from 0.02 to 50, preferably 0.20 to 20, % of the total weight of the mixture.

Lubricants such as aluminum and calcium stearates, talc and silicones, in a concentration of from 0.1 to 5, preferably 0.1 to 3, % of the total weight of the mixture.

Flowability agents such as animal or vegetable fats, especially in hydrogenated form and those which are solid at room temperature. These fats preferably have a melting point of 50° C. or above. Triglycerides of $C_{12}$, $C_{14}$, $C_{16}$ and $C_{18}$ fatty acids are preferred. It is also possible to use waxes such as carnauba wax. These fats and waxes may be admixed advantageously alone or together with mono- and/or diglycerides or phosphatides, especially lecithin. The mono- and diglycerides are preferably derived from the abovementioned fatty acid types. The total amount of fats, waxes, mono-, diglycerides and/or lecithins is from 0.1 to 30, preferably 0.1 to 5, % of the total weight of the composition for each layer.

Dyes, such as azo dyes, organic or inorganic pigments or dyes of natural origin, with preference for inorganic pigments in a concentration of from 0.001 to 10, preferably 0.5 to 3, % of the total weight of the mixture.

Stabilizers such as antioxidants, light stabilizers, hydroperoxide destroyers, radical scavengers, stabilizers against microbial attack.

It is also possible to add wetting agents, preservatives, disintegrants, adsorbents, release agents and propellants (cf., for example, H. Sucker et al., Pharmazeutische Technologie, Thieme-Verlag, Stuttgart 1978).

Auxiliaries include for the purpose of the invention substances for producing a solid solution of the active ingredient. Examples of these auxiliaries are pentaerythritol and pentaerythritol tetraacetate, polymers such as polyethylene oxides and polypropylene oxides and their block copolymers (poloxamers), phosphatides such as lecithin, homo- and copolymers of vinylpyrrolidone, surfactants such as polyoxyethylene 40 stearate, and citric and succinic acids, bile acids, sterols and others as indicated, for example, in J. L. Ford, Pharm. Acta Helv. 61 (1986) 69–88.

Auxiliaries are also regarded as being bases and acids added to control the solubility of an active ingredient (see, for example, K. Thoma et al., Pharm. Ind. 51 (1989) 98–101).

The only precondition for the suitability of auxiliaries is adequate thermal stability.

Active ingredients mean for the purpose of the invention all substances with a physiological effect as long as they do not decompose under the processing conditions. These are, in particular, pharmaceutical active ingredients (for humans and animals), active ingredients for plant treatment, insecticides, active ingredients of human and animal foods, fragrances and perfume oils. The amount of active ingredient per dose unit and the concentration may vary within wide limits depending on the activity and the release rate. The only condition is that they suffice to achieve the desired effect. Thus, the concentration of active ingredient can be in the range from 0.1 to 95, preferably from 20 to 80, in particular 30 to 70, % by weight. It is also possible to employ combinations of active ingredients. Active ingredients for the purpose of the invention also include vitamins and minerals. The vitamins include the vitamins of the A group, the B group, by which are meant besides $B_1$, $B_2$, $B_6$ and $B_{12}$ and nicotinic acid and nicotinamide also compounds with vitamin B properties such as adenine, choline, pantothenic acid, biotin, adenylic acid, folic acid, orotic acid, pangamic acid, carnitine, p-aminobenzoic acid, myo-inositol and lipoic acid, and vitamin C, vitamins of the D group, E group, F group, H group, I and J groups, K group and P group. Active ingredients for the purpose of the invention also include therapeutic peptides. Plant treatment agents include, for example, vinclozolin, epoxiconazole and quinmerac.

The novel process is suitable, for example, for processing the following active ingredients:

acebutolol, acetylcysteine, acetylsalicylic acid, aciclovir, alprazolam, alfacalcidol, allantoin, allopurinol, ambroxol, amikacin, amiloride, aminoacetic acid, amiodarone, amitriptyline, amlodipine, amoxicillin, ampicillin, ascorbic acid, aspartame, astemizole, atenolol, beclomethasone, benserazide, benzalkonium hydrochloride, benzocaine, benzoic acid, betamethasone, bezafibrate, biotin, biperiden, bisoprolol, bromazepam, bromhexine, bromocriptine, budesonide, bufexamac, buflomedil, buspirone, caffeine, camphor, captopril, carbamazepine, carbidopa, carboplatin, cefachlor, cefalexin, cefadroxil, cefazoline, cefixime, cefotaxime, ceftazidime, ceftriaxone, cefuroxime, selegiline, chloramphenicol, chlorhexidine, chlorpbeniramine, chlortalidone, choline, cyclosporin, cilastatin, cimetidine, ciprofloxacin, cisapride, cisplatin, clarithromycin, clavulanic acid, clomipramine, clonazepam, clonidine, clotrimazole, codeine, cholestyramine, cromoglycic acid, cyanocobalamin, cyproterone, desogestrel, dexamethasone, dexpanthenol, dextromethorphsan, dextropropoxiphene, diazepam, diclofenac, digoxin, dihydrdcodeine, dihydroergotamine, dihydroergotoxin, diltiazem, diphenhydramine, dipyridamole, dipyrone, disopyramide, domperidone, dopamine, doxycycline, enalapril, ephedrine, epinephrine, ergocalciferol, ergotamine, erythromycin, estradiol, ethinylestradiol, etoposide, Eucalyptus globulus, famotidine, felodipine, fenofibrate, fenoterol, fentanyl, flavin mononucleotide, fluconazole, flunarizine, fluorouracil, fluoxetine, flurbiprofen, furosemide, gallopamil, gemfibrozil, gentamicin, Gingko biloba, glibenclamide, glipizide, clozapine, Glycyrrhiza glabra, griseofulvin, guaifenesin, haloperidol, heparin, hyaluronic acid, hydrochlorothiazide, hydrocodone, hydrocortisone, hydromorphone, ipratropium hydroxide, ibuprofen, imipenem, indomethacin, iohexol, iopamidol, isosorbide dinitrate, isosorbide mononitrate, isotretinoin, ketotifen, ketoconazole, ketoprofen, ketorolac, labetalol, lactulose, lecithin, levocarnitine, levodopa, levoglutamide, levonorgestrel, levothyroxine, lidocaine, lipase, imipramine, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, multivitamin mixtures or combinations and mineral salts, N-methylephedrine, naftidrofuryl, naproxen, neomycin, nicardipine, nicergoline, nicotinamide, nicotine, nicotinic acid, nifedipine, nimodipine, nitrazepam, nitrendipine, nizatidine, norethisterone, norfloxacin, norgestrel, nortriptyline, nystatin, ofloxacin, omeprazole, ondansetron, pancreatin, panthenol, pantothenic acid, paracetamol, penicillin G. penicillin V, phenobarbital, pentoxifylline, phenoxymethylpenicillin, phenylephrine, phenylpropanolamine, phenytoin, piroxicam, polymyxin B, povidone-iodine, pravastatin, prazepam, prazosin, prednisolone, prednisone, bromocriptine, propafenone, propranolol, proxyphylline, pseudoephedrine, pyridoxine, quinidine, ramipril, ranitidine, reserpine, retinol, riboflavin, rifampicin, rutoside, saccharin, salbutamol, salcatonin, salicylic acid, simvastatin, somatropin, sotalol, spironolactone, sucralfate, sulbactam, sulfamethoxazole, sulfasalazine, sulpiride, tamoxifen, tegafur, teprenone, terazosin, terbutaline, terfenadine, tetracycline, theophylline, thiamine, ticlopidine, timolol, tranexamic acid, tretinoin, triamcinolone acetonide, triamterene, trimethoprim, troxerutin, uracil, valproic acid, vancomycin, verapamil, vitamin E, folinic acid, zidovudine.

Preferred active ingredients are ibuprofen (as racemate, enantiomer or enriched enantiomer), ketoprofen, flurbiprofen, acetylsalicylic acid, verapamil, paracetamol, nifedipine or captopril.

To produce the solid dosage forms, a plastic mixture of the components (melt) is prepared and then subjected to a shaping step. There are various ways of mixing the components and forming the melt. The mixing can take place before, during and/or after the formation of the melt. For example, the components can be mixed first and then melted or be mixed and melted simultaneously. The plastic mixture is often then homogenized in order to disperse the active ingredient thoroughly.

However, it has proven preferable, especially when sensitive active ingredients are used, first to melt the polymeric binder and, where appropriate, make a premix with conventional pharmaceutical additives, and then to mix in (homogenize) the sensitive active ingredient(s) in the plastic phase in intensive mixers with very short residence times. The active ingredient(s) can for this purpose be employed in solid form or in solution or dispersion.

The components are generally employed as such in the production process. However, they can also be used in liquid form, ie. as solution, suspension or dispersion.

Suitable solvents for the liquid form of the components are primarily water or a water-miscible organic solvent or a mixture thereof with water. However, it is also possible to use organic solvents which are immiscible or miscible with water. Suitable water-miscible solvents are, in particular, $C_1$–$C_4$-alkanols such as ethanol, isopropanol or n-propanol, polyols such as ethylene glycol, glycerol and polyethylene glycols. Suitable water-immiscible solvents are alkanes such as pentane or hexane, esters such as ethyl acetate or butyl acetate, chlorinated hydrocarbons such as methylene chloride, and aromatic hydrocarbons such as toluene and xylene. Another solvent which can be used is liquid $CO_2$.

The solvent used in the individual case depends on the component to be taken up and the properties thereof. For example, pharmaceutical active ingredients are frequently used in the form of a salt which is, in general, soluble in water. Water-soluble active ingredients can therefore be employed as aqueous solution or, preferably, be taken up in the aqueous solution or dispersion of the binder. A corresponding statement applies to active ingredients which are soluble in one of the solvents mentioned, if the liquid form of the components used is based on an organic solvent.

It is possible where appropriate to replace melting by dissolving, suspending, or dispersing in the abovementioned solvents, if desired and/or necessary with the addition of suitable auxiliaries such as emulsifiers. The solvent is then generally removed to form the melt in a suitable apparatus, eg. an extruder. This will be comprised by the term mixing hereinafter.

The melting and/or mixing takes place in an apparatus customary for this purpose. Particularly suitable ones are extruders or containers which can be heated where appropriate and have an agitator, eg. kneaders (like those of the type to be mentioned below).

A particularly suitable mixing apparatus is one employed for mixing in plastics technology. Suitable apparatuses are described, for example, in "Mischen beim Herstellen und Verarbeiten von Kunststoffen", H. Pahl, VDI-Verlag, 1986. Particularly suitable mixing apparatuses are extruders and dynamic and static mixers, and stirred vessels, single-shaft stirrers with stripper mechanisms, especially paste mixers, multishaft stirrers, especially PDSM mixers, solids mixers and, preferably, mixer/kneader reactors (eg. ORP, CRP, AP, DTB supplied by List or Reactotherm supplied by Krauss-Maffei or Ko-Kneter supplied by Buss), trough mixers and internal mixers or rotor/stator systems (eg. Dispax supplied by IKA).

In the case of sensitive active ingredients it is preferable first for the polymeric binder to be melted in an extruder and then for the active ingredient to be admixed in a mixer/ kneader reactor. On the other hand, with less sensitive active ingredients, a rotor/stator system can be employed for vigorously dispersing the active ingredient.

The mixing apparatus is charged continuously or batchwise, depending on its design, in a conventional way. Powdered components can be introduced in a free feed, eg. via a weigh feeder. Plastic compositions can be fed in directly from an extruder or via a gear pump, which is particularly advantageous if the viscosities and pressures are high. Liquid media can be metered in by a suitable pump unit.

The mixture obtained by mixing and/or melting the binder, the active ingredient and, where appropriate, the additives) ranges from pasty to viscous (plastic) or fluid and is therefore extrudable. The glass transition temperature of the mixture is below the decomposition temperature of all the components present in the mixture. The binder should preferably be soluble or swellable in a physiological medium.

The steps of mixing and melting in the process can be carried out in the same apparatus or in two or more separately operating apparatuses. The preparation of a premix can take place in one of the conventional mixing apparatuses described above. A premix of this type can then be fed directly, for example, into an extruder and subsequently extruded, where appropriate with the addition of other components.

It is possible in the novel process to employ as extruders single screw machines, intermeshing screw machines or else multiscrew extruders, especially twin screw extruders, corotating or counterrotating and, where appropriate, equipped with kneading disks. If it is necessary in the extrusion to evaporate a solvent, the extruders are generally equipped with an evaporating section. Particularly preferred extruders are those of the ZSK series from Werner & Pfleiderer.

It is also possible according to the invention to produce multilayer pharmaceutical forms by coextrusion, in which case a plurality of mixtures of the components described above is fed together to an extrusion die so as to result in the required layered structure of the multilayer pharmaceutical form. It is preferable to use different binders for different layers.

Multilayer drug forms preferably comprise two or three layers. They may be in open or closed form, in particular as open or closed multilayer tablets.

At least one of the layers contains at least one pharmaceutical active ingredient. It is also possible for another active ingredient to be present in another layer. This has the advantage that two mutually incompatible active ingredients can be processed or that the release characteristics of the active ingredient can be controlled.

The shaping takes place by coextrusion with the mixtures from the individual extruders or other units being fed into a common coextrusion die and extruded. The shape of the coextrusion die depends on the required pharmaceutical form. Examples of suitable dies are those with a flat orifice, called a slit die, and dies with an annular orifice. The design of the die depends on the polymeric binder used and the required pharmaceutical form.

The resulting mixture is preferably solvent-free, ie. it contains neither water nor an organic solvent.

The plastic mixture is, as a rule, subjected to final shaping. This can result in a large number of shapes depending on the die and mode of shaping:. For example, if an extruder is used, the extrudate can be shaped between a belt and a roll, between two belts or between two rolls, as described in EP-A-358 105, or by calendering in a calender with two molding rolls, see, for example, EP-A-240 904. Other shapes can be obtained by extrusion and hot- or cold-cut of the extrudate, for example small-particle and uniformly shaped pellets. Hot-cut pelletization usually results in lenticular dosage forms (tablets) with a diameter of from 1 to 10 mm, while strip pelletization normally results in cylindrical products with a length to diameter ratio of from 1 to 10 and a diameter of from 0.5 to 10 mm. It is thus possible to produce monolayer but also, on use of coextrusion, open or closed multilayer dosage forms, for example oblong tablets, coated tablets, pastilles and pellets. The resulting granules can then also be ground to a powder and compressed to tablets in a conventional way. Micropastilles can be produced by the Rotoform-Sandvik process. These dosage forms can be rounded and/or provided with a coating by conventional methods in a subsequent process step. Examples of materials suitable for film coatings are polyacrylates such as the Eudragit types, cellulose esters such as the hydroxypropylcellulose phthalates, and cellulose ethers, such as ethylcellulose, hydroxypropylmethylcellulose or hydroxypropylcellulose.

In specific cases there may be formation of solid solutions. The term solid solutions is familiar to the skilled worker, for example from the literature cited at the outset. In solid solutions of active ingredients in polymers, the active ingredient is in the form of a molecular dispersion in the polymer.

The following examples are intended to illustrate the novel process without restricting it, however.

EXAMPLES

Example 1

Synthesis of a Graft Copolymer Consisting of 40% by Weight of an Oxygen-Containing Block Copolymer (Grafting Base) and 60% by Weight of Methyl Methacrylate (Grafted-On Monomer)

A mixture of 240 g of an ABA block copolymer (Poloxamer 188; A polyethylene oxide block, B=polypropylene oxide block) and 440 g of n-propanol was heated to 92° C. while stirring under a nitrogen atmosphere. After the internal temperature reached 92° C., 70 g of methyl methacrylate and 21 g of a mixture of 3 g of tert-butyl peroctoate and 120 g of n-propanol were added. Then, while stirring continuously at 92° C., 290 g of methyl methacrylate were metered in over 2 hours and the remainder of the mixture of 3 g of tert-butyl peroctoate and 120 g of n-propanol was metered in over 2.5 hours. After the initiator had been fed in, the mixture was refluxed for two hours and, after addition of a further 0.6 g of tert-butyl peroctoate, after-polymerization was carried out under reflux for 3 hours. 600 g of water were added, and the reaction mixture was cooled overnight. The next morning the n-propanol was replaced by water (steam distillation) and the precipitated product was filtered off (suction funnel) and washed with a large amount of water. A white powder was obtained. K value (1% strength in acetone): 22.9; DSC: 1 glass transition stage at 58° C. (2nd heating cycle).

Example 2

Synthesis of a Graft Copolymer Consisting of 30% by Weight of an Oxygen-Containing Block Copolymer (Grafting Base) and 70% by Weight of Methyl Methacrylate (Grafted-On Monomer)

A mixture of 180 g of an ABA block copolymer (Poloxamer 188; A polyethylene oxide block, B=polypropylene oxide block) and 440 g of n-propanol was heated to 92° C. while stirring under a nitrogen atmosphere. After the internal temperature reached 92° C., 70 g of methyl methacrylate and 21 g of a mixture of 3 g of tert-butyl peroctoate and 120 g of n-propanol were added. Then, while stirring continuously at 92° C., 350 g of methyl methacrylate were metered in over 2 hours and the remainder of the mixture of 3 g of tert-butyl peroctoate and 120 g of n-propanol was metered in over 2.5 hours. After the initiator had been fed in, the mixture was refluxed for two hours and, after addition of a further 0.6 g of tert-butyl peroctoate, after-polymerization was carried out under reflux for 3 hours. 600 g of water were added, and the reaction mixture was cooled overnight. The next morning the n-propanol was replaced by water (steam distillation) and the precipitated product was filtered off (suction funnel) and washed with a large amount of water. A white powder was obtained. K value (1% strength in acetone): 29.1; DSC: 1 glass transition stage at 67° C. (2nd heating cycle).

Example 3

Synthesis of a Graft Copolymer Consisting of 20% by Weight of an Oxygen-Containing Block Copolymer (Grafting Base) and 80% by Weight of Methyl Methacrylate (Grafted-On Monomer)

A mixture of 120 g of the ABA block copolymer from Example 1 (A=polyethylene oxide block, B=polypropylene oxide block) and 440 g of n-propanol was heated to 92° C. while stirring under a nitrogen atmosphere. After the internal temperature reached 92° C., 70 g of methyl methacrylate and 21 g of a mixture of 3 g of tert-butyl peroctoate and 120 g of n-propanol were added. Then, while stirring continuously at 92° C., 410 g of methyl methacrylate were metered in over 2 hours and the remainder of the mixture of 3 g of tert-butyl peroctoate and 120 g of n-propanol was metered in over 2.5 hours. After the initiator had been fed in, the mixture was refluxed for two hours and, after addition of a further 0.6 g of tert-butyl peroctoate, after-polymerization was carried out under reflux for 3 hours. 600 g of water were added, and the reaction mixture was cooled overnight. The next morning the n-propanol was replaced by water (steam distillation) and the precipitated product was filtered off (suction funnel) and washed with a large amount of water. A white powder was obtained. K value (1% strength in acetone): 30.2; DSC: 1 glass transition stage at 78° C. (2nd heating cycle).

Example 4

520 g of the Graft Copolymer from Example 1 were Extruded with 480 g of Verapamil Hydrochloride, and Calendered to 1000 mg Oblong Tablets, Under the Following Conditions Section 1 67° C.
Section 2 98° C.
Section 3 131° C.
Section 4 111° C.
Section 5 97° C.
Die 81° C.

The release after 8 hours was 40% [USP paddle method (pH change)].

Example 5

520 g of the Graft Copolymer from Example 2 Were Extruded with 480 g of Verapamil Hydrochloride, and Calendered to 1000 mg Oblong Tablets, Under the Following Conditions Section 1 63° C.
Section 2 96° C.
Section 3 131° C.
Section 4 110° C.
Section 5 97° C.
Die 90° C.

The release after 8 hours was 45% [USP paddle method (pH change)].

Example 6

520 g of the Graft Copolymer from Example 3 Were Extruded with 480 g of Verapamil Hydrochloride, and Calendered to 1000 mg Oblong Tablets, Under the Following Conditions Section 1 56° C.
Section 2 92° C.
Section 3 130° C.
Section 4 112° C.
Section 5 100° C.
Die 90° C.

The release after 8 hours was 47% USP paddle method (pH change)].

We claim:

1. A process for producing a solid dosage form by mixing at least one polymer binder, at least one active ingredient and optionally conventional additives to form a plastic mixture, and shaping the plastic mixture, wherein the polymeric binder is a water-swellable graft copolymer which is obtained by free radical initiated polymerization of
   a) $C_1$–$C_{30}$-alkyl esters, hydroxy-$C_2$–$C_4$-alkyl esters, amides, mono- or di-$C_1$–$C_4$-alkylamides or nitriles of monoethylenically unsaturated $C_3$–$C_{30}$-mono- or dicarboxylic acids or mixtures thereof in the presence of
   b) homo- or copolymers of $C_2$–$C_4$-alkylene oxides as grafting base, and
   c) optionally one or more monomers having at least two non-conjugated ethylenically unsaturated double bonds, and wherein component a) optionally comprises up to 5% by weight, based on the total weight of component a), of an α,β-monoethylenically unsaturated $C_3$–$C_8$-carboxylic acid.

2. The process of claim 1, wherein component a) of the graft copolymer is at least one ester of acrylic acid or methacrylic acid with a $C_1$–$C_8$-alkanol.

3. The process of claim 1, wherein the graft copolymer comprises components a) and b) in a ratio of from 95 to 10:5 to 90 by weight.

4. The process of claim 3, wherein the ratio is of from 85 to 55:15 to 45 by weight.

5. The process of claim 1, wherein the graft copolymer has a Fikentscher K value of from 7 to 100.

6. The process of claim 5, wherein the Fikentscher K value is of from 20 to 35.

7. The process of claim 1, wherein the plastic mixture is formed by mixing and/or melting the components in an extruder.

8. The process of claim 1, wherein the dosage form is adapted as a pharmaceutical dosage form, a fragrance formulation, a plant treatment composition, an animal feed additive or supplement, or a human food supplement.

9. The process of claim 1, wherein component b) of the graft copolymer is a homo- or copolymer of ethylene oxide, propylene oxide, n-butylene oxide or isobutylene oxide.

10. The process of claim 1, wherein component a) is methyl methacrylate and component b) is a copolymer of ethylene oxide and propylene oxide.

* * * * *

UNITED STATES PATENT AND TRADEMARK OFFICE
CERTIFICATE OF CORRECTION

PATENT NO. : 7,022,344 B2  
DATED : April 4, 2006  
INVENTOR(S) : Kothrade et al.

Page 1 of 1

It is certified that error appears in the above-identified patent and that said Letters Patent is hereby corrected as shown below:

Column 12,  
Line 29, "$C_l$-$C_{30}$-alkyl esters" should read -- $C_1$-$C_{30}$-alkyl esters --.  
Line 31, "nitrites" should read -- nitriles --.

Signed and Sealed this

Sixth Day of June, 2006

JON W. DUDAS  
*Director of the United States Patent and Trademark Office*